United States Patent

Whisson

[11] Patent Number: 5,562,635
[45] Date of Patent: Oct. 8, 1996

[54] PARENTERAL DEVICE

[75] Inventor: Maxwell E. Whisson, Nedlands, Australia

[73] Assignee: Eastland Technology Australia Pty Ltd, West Perth, Australia

[21] Appl. No.: 313,059
[22] PCT Filed: Apr. 21, 1993
[86] PCT No.: PCT/AU93/00175
§ 371 Date: Jan. 18, 1995
§ 102(e) Date: Jan. 18, 1995
[87] PCT Pub. No.: WO93/20872
PCT Pub. Date: Oct. 28, 1993

[30] Foreign Application Priority Data

Apr. 21, 1992 [AU] Australia ............... PL1986

[51] Int. Cl.⁶ ............................................. A61M 5/32
[52] U.S. Cl. ............................ 604/195; 604/110; 604/89
[58] Field of Search ........................ 604/110, 187, 604/232–234, 86, 88, 89, 90, 157, 194–198, 218, 228, 263

[56] References Cited

U.S. PATENT DOCUMENTS

| | | |
|---|---|---|
| 2,475,060 | 7/1949 | Smith . |
| 2,833,280 | 5/1958 | Hein, Jr. ............................. 604/89 |
| 3,368,558 | 2/1968 | Sarnoff et al. . |
| 3,587,575 | 6/1971 | Lichtenstein . |
| 4,850,968 | 7/1989 | Romano ............................. 604/110 |
| 4,874,382 | 10/1989 | Lindemann et al. ................ 604/195 |
| 4,908,022 | 3/1990 | Haber . |
| 5,007,903 | 4/1991 | Ellard ................................. 604/195 |
| 5,267,961 | 12/1993 | Shaw ................................. 604/110 |
| 5,290,256 | 3/1994 | Weatherford et al. ............. 604/198 |
| 5,403,289 | 4/1995 | Berrebi et al. .................... 604/232 |

FOREIGN PATENT DOCUMENTS

| | | |
|---|---|---|
| 0326983 | 8/1989 | European Pat. Off. . |
| 2064964A | 6/1981 | United Kingdom . |
| WO90/05555 | 5/1990 | WIPO . |
| WO91/00747 | 1/1991 | WIPO . |
| WO91/00751 | 1/1991 | WIPO . |

Primary Examiner—Randall L. Green
Assistant Examiner—V. Alexander
Attorney, Agent, or Firm—Merchant, Gould, Smith, Edell, Welter & Schmidt, P.A.

[57] ABSTRACT

A parenteral device (10) comprising a body (12) having a forward end (26) and a rearward end (34). The forward end (26) is capable of receiving a hollow retractable needle (20) therein so as to project therefrom. The retractable needle (20) is slidable relative to the body (12) and the body (12) also includes a chamber (14) capable of receiving parenteral fluid and capable of being reduced in volume to expel fluid contained therein. The needle (20) is capable of being manually retracted within the body (12) such that the chamber (14) reduces in volume to expel fluid contained therein and such that the needle (20) is retracted to be wholly contained within the body (12).

10 Claims, 1 Drawing Sheet

US 5,562,635

PARENTERAL DEVICE

FIELD OF THE INVENTION

This invention relates to an improved parenteral device.

BACKGROUND OF THE INVENTION

Throughout this specification the term "parenteral device" shall be taken to include any device which can be used for the conveyance of parenteral fluids which are to be introduced into or drawn from the body through the skin and shall include within its scope a syringe, a cannula, a hypodermic needle, an intravenous infusion line, and like devices.

A primary characteristic of parenteral devices is the provision of a sharp hollow needle to facilitate the transfer of fluids to or from the body. The difficulty created by the presence of such a needle arises from the possibility of injury which may be caused to a user or to medical staff when using the device, or indeed to any person who may be required to handle the device before or after use.

Of course, the injury itself does not represent the major concern; the major concern arises from the dangers of infection from such injuries due to the presence of pathogens which may be present on the needle as a result of its use. Indeed, it has been proven that a number of viral infections, notably the HIV virus and hepatitis B, can be transmitted by the reuse of needles previously used to inject an infected individual.

These dangers have resulted in the development of very careful and sometimes detailed disposal procedures being adopted in institutions where such parenteral devices are used. It has also resulted in attempts being made at developing single use parenteral devices that are not capable of being reused.

However, the disposal procedures adopted by such institutions are not able to be enforced in out-of-clinic situations, such as those situations where individuals inject recreational drugs. Further, the users of recreational drugs are often capable of quite easily manipulating a so called "one use" syringe to be able to continue using that same syringe.

SUMMARY OF THE INVENTION

It is an object of the present invention to provide an improved parenteral device wherein operation of the device in performing an injection alters the configuration of the device such that the device becomes extremely difficult to refill and also to reuse. A further object is to provide a parenteral device having a needle that retracts so as not to be exposed after use.

The present invention provides a parenteral device comprising a body having a forward end and a rearward end, the forward end being capable of receiving a hollow retractable needle therein so as to project therefrom, the retractable needle being slidable relative to the body, the body also including a chamber capable of receiving parenteral fluid and capable of being reduced in volume to expel fluid contained therein, wherein the needle is capable of being manually retracted within the body such that the chamber reduces in volume to expel fluid contained therein and such that the needle is retracted to be wholly contained within the body.

The retractable needle is preferably mounted in a plug, the plug being configured so as to sealingly engage with the internal walls of the body but to be slidable relative thereto. The chamber is preferably located rearwardly of the plug such that the needle then projects through the plug to provide fluid communication with the chamber at the rear thereof and the hollow interior of the needle.

Thus, by actuating the parenteral device to slide the plug towards the rear of the body, the volume of the chamber is reduced and fluid is expelled therefrom through the hollow needle. At the same time, the needle itself is retracting within the body. With this mode of operation, the parenteral device is preferably configured such that the full dose of parenteral fluid to be injected below the skin has been delivered before the sharp end of the needle is removed from below the skin. Preferably the full dose has been delivered prior to the sharp end of the needle retracting to a depth of about 5 mm below the skin.

Indeed, by holding the body of the parenteral device closely adjacent the skin of the user, the needle may continue to be retracted within the body of the device such that the sharp end of the needle is not exposed whatsoever between insertion and completion of the injection.

When using the parenteral device of this invention it thus becomes important to use the device accurately to ensure that the dose is delivered subcutaneously. However, in a preferred form of the invention, a stopping means is provided to define the rear extent of the initial movement of the plug and also to define the rear end of the chamber.

In order to prevent the sharp end of the needle being left exposed at its fully retracted position the stopping means is also preferably slidable relative to the body and is in sealing engagement with the internal walls of the body. Thus, the initial retracting of the needle causes the volume of the chamber to reduce so as to expel the fluid therefrom, to a point where the plug abuts the stopping means. Further retraction of the needle then forces the rearward movement of the stopping means to allow all of the needle to be withdrawn inside the body. Preferably, a greater degree of force is required to move the stopping means than to expel the fluid.

The retracting means is preferably an externally operable means secured either directly or indirectly to the plug. For example, the retracting means may be a flexible line located internally of the body of the parenteral device, secured to the rear surface of the plug and passing sealingly through the stopping means. The line preferably passes through the stopping means via a sealable aperture such that the plug may be pulled through the stopping means to urge the plug rearwardly and cause the initial retraction of the needle. Of course, it will be appreciated that other manual retraction means may be utilised.

Therefore, the present invention also provides a parenteral device comprising a body having a forward end and a rearward end, the forward end being capable of receiving a hollow retractable needle therein so as to project therefrom, the retractable needle being slidable relative to the body, the body also including a chamber capable of receiving parenteral fluid and capable of being reduced in volume to expel fluid contained therein, wherein: the needle is capable of being manually retracted within the body such that the chamber reduces in volume to expel fluid contained therein and such that the needle is retracted to be wholly contained within the body; the retractable needle is mounted in a plug, the plug being configured so as to sealingly engage with the internal walls of the body but to be slidable relative thereto; the chamber is located rearwardly of the plug such that the needle projects through the plug to provide fluid communication with the chamber at the rear thereof and the hollow interior of the needle; a stopping means is provided to define the rear extent of the movement of the plug and also to define the rear end of the chamber, the stopping means being slidable relative to the body and being in sealing engagement with the internal walls of the body such that a greater degree of force is required to move the stopping means than to move the plug and thus expel the fluid; and the retracting means is a flexible line located internally of the body of the parenteral device, secured to the rear surface of the plug and passing through the stopping means.

It may be possible to fill the chamber of the parenteral device in a number of ways and using a variety of alternative configurations. In one form, the parenteral device may be provided with the plug abutting the stopping means such that the sharp end of the needle projects beyond the forward end of the body of the device, the sharp end being covered and protected by a protective external tube. The tube preferably has lateral projections located at or near its rearward end and is of a form such that the tube is able to pass easily through the opened end of a standard glass or plastic parenteral medication ampoule or vial, but being of a configuration such that the lateral projections may be easily caught against the inner shoulders of such an ampoule or vial, offering resistance when the needle, to which the tube is attached, is gently pulled. Thus, by pulling the body of the parenteral device away from the ampoule or vial, the volume of the chamber progressively increases, drawing fluid via the tube through the hollow needle into the chamber. Preferably, the firmness of the attachment of the tube to the needle is arranged such that a greater force will pull the needle from within the tube, leaving the tube discarded within the ampoule. The parenteral device is then loaded with parenteral fluid ready for use.

In another form, the protective tube referred to above may be formed of a fairly hard plastic, such as polycarbonate, or even of metal, and may be of sufficiently small end section that it can be pushed through an elastic bung such as is normally fitted to glass vials as a closure. In this form, the lateral projections of the protective tube are in the form of a flange located at the rearward end of the tube so as to lie adjacent the barrel when the parenteral device is supplied in its empty state. Force may then be exerted on the barrel to cause the tube to penetrate the elastic bung. An opposite force may then be applied to allow passage of parenteral fluid through the tube, through the needle, and into the chamber when the plug is moved forwardly to increase the volume of the chamber. Removal of the tube from the needle may be facilitated by ratchet shaped ridges formed on the tube causing resistance to withdrawal of the tube from the vial. Additionally, an expanded flange may be provided such as to allow the operator to simply remove the tube with fingertip pressure.

It can thus be seen that the present invention provides an improved parenteral device that allows for the complete retraction of its needle during use within the body thereof. The lack of any externally extending rigid pieces that may allow the re-extension of the needle assists in causing the device to be primarily a one use device. The construction of the device is simple and cheap and allows for relatively easily filling with minimal complexity. Further, it is expected that as the injection of parenteral fluid and withdrawal of the needle occurs simultaneously, there may be the additional beneficial effect of depositing the parenteral fluid throughout the deeper part of the needle track. This is expected to have advantages in reduction of pain due to distension of tissues and more rapid absorption of the fluid.

It will also be appreciated that the dimensions and extent of travel of the needle and plug may be optimised for expelling a parenteral fluid into any body cavity. In particular, the needle may be inserted into a vein and retracted along the lumen of the vein as the parenteral fluid is expelled, the chamber being completely emptied before the needle is retracted out of the vein.

The present invention will now be described in relation to the accompanying drawings. However, it is to be appreciated that the following description is not to limit the generality of the above description.

DETAILED DESCRIPTION OF THE PREFERRED EMBODIMENTS

Figure 1:
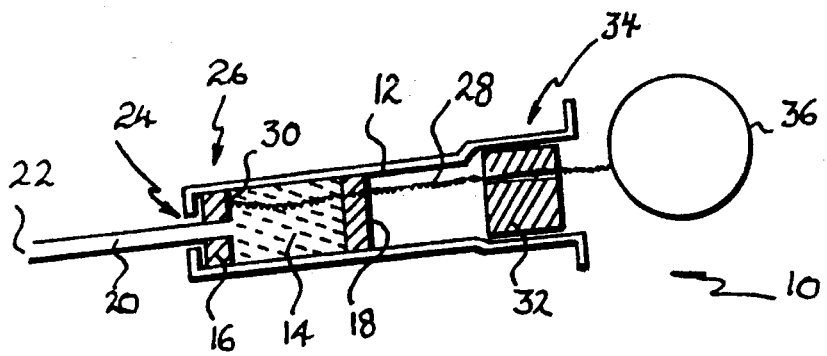
FIG. 1 is a sectional view of a parenteral device according to a first embodiment of the present invention.

FIG. 1 illustrates a parenteral device 10 having a body 12 in the form of a substantially tubular barrel which provides a sealed chamber 14 between a plug 16 and a stopping means 18. A sharpened tubular needle 20 is firmly fixed to the plug 16 and passes therethrough so as to provide fluid communication within the hollow interior of the needle 20 between the chamber 14 and the open end 22 of the needle 20. The needle 20 passes through an opening 24 in the forward end 26 of the body 12.

A retracting means in the form of a drawstring 28 is secured to the rear surface 30 of the plug 16. The drawstring 28 passes through the stopping means 18 in sealing engagement therewith and also passes through a second plug 32 secured in the rearward end 34 of the body 12. The passage of the drawstring 28 through the second plug 32 is preferably a loose fit.

The chamber 14 is capable of receiving and containing a parenteral fluid such that by pulling the drawstring 28 via finger loop 36, the plug 16 is urged to the rear of the body 12, thus retracting the needle 20 and reducing the volume of the chamber 14 to expel the parenteral fluid through the needle 20 and out the open end 22 thereof.

Figure 2:
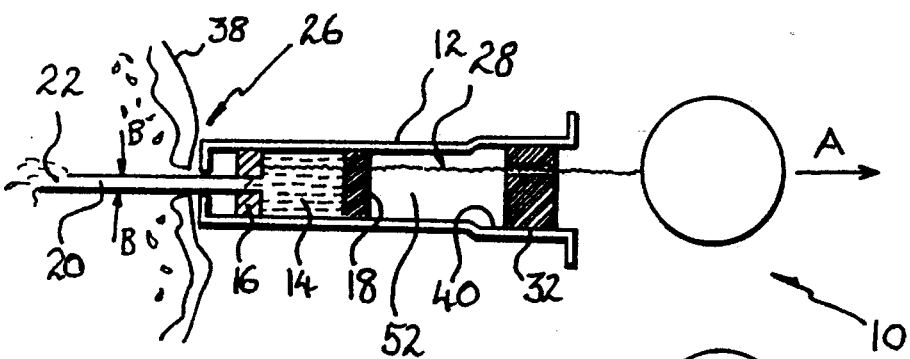
FIG. 2 is a sectional view of the embodiment of FIG. 1 in use.

The device 10 is shown in use in FIG. 2 with the needle 20 having been inserted below the surface of the skin 38 of a person. With the parenteral device 10 in this position, with its forward end 26 closely adjacent the skin 38, the drawstring 28 may be pulled in the direction of arrow A to reduce the volume of chamber 14 by urging the plug 16 towards the stopping means 18 to expel the parenteral fluid from the needle 20. As this occurs, the needle 20 is being withdrawn within the body 12 of the device 10. In this form, the device 10 is preferably configured such that all of the parenteral fluid is expelled from the chamber 14 by the time that the open end 22 of the needle 20 reaches point B which is about 5 mm below the surface of the skin 38.

Figure 3:
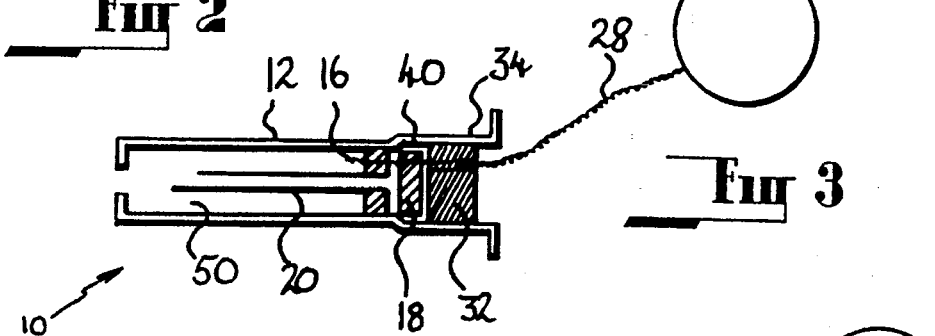
FIG. 3 is a sectional view of the embodiment of FIG. 1 after use.

FIG. 3 illustrates the device 10 after all of the parenteral fluid has been expelled from the chamber 14 and after the needle 20 has been retracted completely within the body 12. In this respect, the drawstring 28 has been pulled through the stopping means 18 to a point where the chamber 14 has been reduced in volume to be substantially zero and the plug 16 is in contact with the stopping means 18. On the application of a further force to the drawstring 28 the slidable stopping means 18 is urged towards the rear 34 of the body 12 such that the entire length of the needle 20 is retracted within the body 12. Further, each of FIGS. 2 and 3 illustrate a region or rear portion 40 of increased diameter within which the stopping means 18 is able to be loosely received. Of course, the second plug 32 is also received within that region 40 of increased diameter.

There being no rigid, externally extending projection on the plug 16, it is not possible for a user to realign the plug 16 and the needle 20 to reuse the syringe. Further, if the plug and needle do happen to be able to be realigned, the lack of a seal between the stopping means 18 and the internal walls of the body 12, together with the lack of a sealing engagement between the drawstring 28 and the second plug 32, results in the user being unable to refill a syringe.

Further, it is possible to integrally include with the inner wall of the body 12 sharp internal projections which are able to damage the sealing surfaces of the stopping means 18. Alternatively, a spike or the like may be fitted to the second plug 32 to pierce the stopping means 18, again to destroy the sealing capacity of the stopping means 18. Further still, the drawstring 28 may pass through the stopping means 18 eccentrically or at an angle such that when the stopping means 18 reaches the increased diameter portion of the body 12 it tilts so that its sealing surfaces are no longer properly aligned.

In a further preferred form, the increased diameter portion may be of a size that is also capable of receiving the plug. This would further assist in rendering the parenteral device of the invention unusable after its initial use. Further, the reduced diameter portion may be defined by a sharp reduction in diameter, so as to provide a well defined shoulder, or by a smoothly increasing portion in the form of a gradual taper increasing in diameter towards the rear of the body of the device, or by another suitable configuration as necessary.

Figure 4:
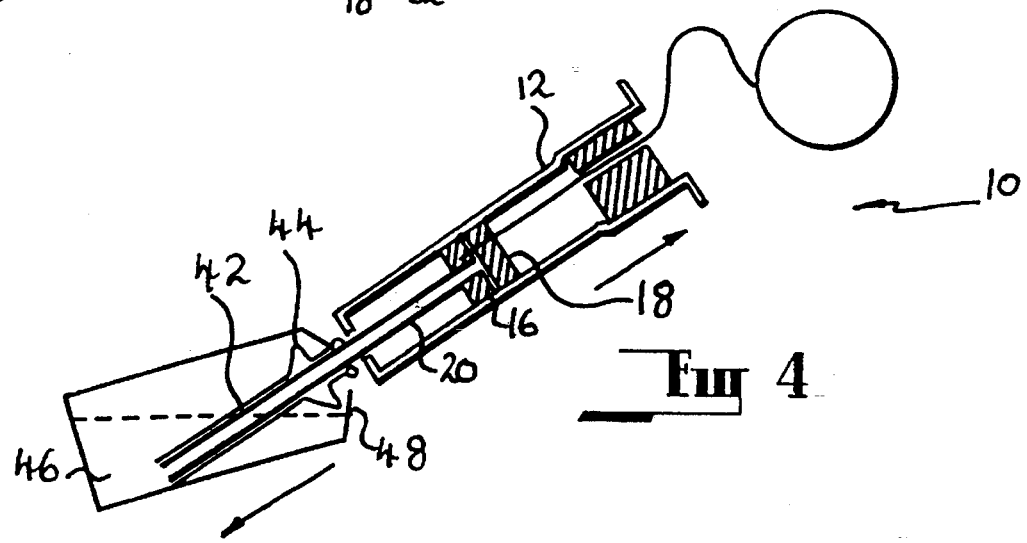
FIG. 4 is a sectional view of the embodiment of FIG. 1 prior to filling.

Illustrated in FIG. 4 is an example of a manner in which the parenteral device 10 of the present invention may be filled. In FIG. 4 the needle 20 of the device 10 is covered at its sharp end by a protective tube 42 having lateral projections 44 located at or near its rearward end. The lateral projections 44 are preferably configured so as to allow the tube 42 to be easily placed within an open ampoule or vial so as to be able to insert the forward end of the tube within the parenteral fluid 46 within the vial. However, the lateral projections 44 are also configured so as to be capable of abutting the neck portions 48 of the ampoule or vial to grip the tube therewithin. Thus, by the user gripping the body 12 of the device 10 and locating the lateral projections 44 against the neck portions 48 of the ampoule or vial, the plug 16 and the stopping means 18 may be urged to part, creating the chamber 14 (not yet visible in FIG. 4) and the reduction in pressure within that newly created chamber causes the fluid 46 to transfer through the tube 42, through the needle 20 and into the chamber.

The tight fit of the needle 20 within the tube 42 is preferably only such as to allow a gentle force to be applied thereto to allow the filling of the chamber. However, on application of a greater force, the needle 20 may be withdrawn from within the tube 42 to allow use of the needle.

As indicated above, further adaptions may be made to the tube 42 to allow it, or a similar device, to be used to fill the device 10 of the present invention from any known type of supply of parenteral fluid. Further, the tube or its equivalents may be provided with means for the user to grip the tube to remove the tube manually rather than rely on mechanical actions to remove the tube.

In an alternative form, and referring to FIG. 3, it may be preferred to adapt the device 10 of the present invention to include a spring, or a like resilient device, within the space 50 forward of the plug 16. For example, a spring that is contracted to fill the chamber 14 with parenteral fluid and thus expands under its normal bias to reduce the volume of the chamber 14, may be suitable. Of course, a trigger mechanism would then be provided to hold the spring in its contracted position and to allow the release and subsequent expansion of the spring for injection. For example, a trigger mechanism may be located externally of the device and may connect with the spring through the forward wall of the body of the device.

It will be appreciated that other types of externally located retracting means may be utilised in substitution for the drawstring shown in the drawings. It will also be appreciated that the resilient device referred to above may alternatively be located within a space 52 located rearward of the plug 16 (see FIG. 2). In this alternative form, the resilient device may be a spring configured so as to expand to fill the chamber 14 with parenteral fluid and then to contract under its normal bias to reduce the volume of the chamber and expel the fluid. In such an arrangement, the drawstring referred to above may be secured to one end of the spring such that contraction of the spring moves the one end of the spring rearwardly to pull the plug rearwardly. Further, the spring is preferably configured so as to also displace the stopping means in the same manner as described above. An appropriate trigger mechanism may again be utilised to control the actions of this rearwardly located spring.

Finally, the parenteral device of this invention may be marked with external graduations, according to normal practice, to assist in ensuring the administration of correct doses of parenteral fluid. This normal practice results in graduations from zero to a suitable number being included from the forward end of the device to the rearward end.

However, due to the manner in which the parenteral device of this invention functions, there is less risk of the user injecting an incorrect dose. In this respect, a traditional syringe capable of holding, for example, 5 ml of fluid would often be used to administer, for example 3 ml of fluid. In this instance, the user would fill the syringe to 5 ml but would then move the plunger to expel fluid from 5 ml back-to the marking of 2 ml on the graduations in order to expel 3 ml of fluid. It would thus be possible for the user to incorrectly believe that the plunger should only be moved back to the 3 ml marking on the graduations, and fall short of expelling the correct dose.

In the parenteral device of the present invention, the plug would move from the zero graduation through to the 3 ml marking on the graduations to give a direct representation of the dose administered.

It will be appreciated that there may be other modifications and variations that may be made to the configurations described herein that are also within the scope of the present invention.

I claim:

1. A parenteral device comprising:

a hollow elongate body having a forward end and a rearward end;

a plug slidably and sealingly supported in the body;

a hollow needle supported from the plug so as to project forwardly therefrom;

a stop supported in the body rearwardly of the plug;

a chamber formed between the plug and stop for receiving parenteral fluid and being reduced in volume to expel fluid contained therein, wherein said needle projects through the plug to provide fluid communication between the chamber and the hollow interior of the needle; and a retraction means located rearwardly of the stop and connected to the plug for moving the plug rearwardly towards the stop to retract the needle within the body while expelling fluid contained in the chamber such that the needle is retracted to be wholly contained within the body.

2. A parenteral device according to claim 1 wherein the stop defines the rear extent of an initial rearward movement of the plug.

3. A parenteral device according to claim 2 wherein the stop is slidable relative to the body.

4. A parenteral device according to claim 3 wherein a greater force is required to move the stop than to move the plug.

5. A parenteral device according to claim 1 wherein the retraction means is a flexible elongate member located internally of the body, having a handle extending from the rearward end of the body, and secured at the other end to the plug and slidably and sealingly received through the stop.

6. A parenteral device according to claim 1 wherein the body includes a rear portion located rearward of the stop, said rear portion having an increased dimension to be capable of non-sealingly receiving the stop.

7. A parenteral device according to claim 7 wherein the junction between the body and the rear portion is defined by a sudden increase in diameter.

8. A parenteral device comprising a hollow elongate body having a forward end and a rearward end, the body slidably and sealingly supporting a plug, a needle supported from the plug to project forwardly therefrom, a stop slidably and sealingly supported in the body rearward of the plug to define a chamber between the plug and the stop, the stop being in sealing engagement with the internal walls of the body such that a greater degree of force is required to move the stop than to move the plug, wherein:

a retraction means is connected to the plug for manually retracting the needle within the body such that the chamber reduces in volume to expel parenteral fluid contained therein and such that the needle is retracted to be wholly contained within the body;

the needle projects through the plug to provide fluid communication with the chamber and the hollow interior of the needle;

and the retraction means comprises a flexible elongate member located internally of the body of the parenteral device, secured to the plug and passing through the stop.

9. A parenteral device according to claim 8 wherein the body includes a rear portion located rearward of the stop, said rear portion having an increased dimension for non-sealingly receiving the stop.

10. A parenteral device according to claim 9 wherein the junction between the body and the rear portion is defined by a sudden increase in diameter.

* * * * *